(12) United States Patent
Weiland et al.

(10) Patent No.: US 6,371,987 B1
(45) Date of Patent: Apr. 16, 2002

(54) DEVICE FOR CONNECTING VERTEBRAE OF THE VERTEBRAL COLUMN

(75) Inventors: Peter Weiland, Nonnweiler-Braunshausen; Hans-Joachim Wilke, Ulm, both of (DE)

(73) Assignee: Medinorm AG Medizintechnische Produkte, Quierschied (DE)

( * ) Notice: Subject to any disclaimer, the term of this patent is extended or adjusted under 35 U.S.C. 154(b) by 0 days.

(21) Appl. No.: 09/293,406

(22) Filed: Apr. 16, 1999

(30) Foreign Application Priority Data

Apr. 23, 1998 (DE) .......................... 198 18 143

(51) Int. Cl.⁷ .................................................. A61F 2/44
(52) U.S. Cl. .................................................. 623/17.11
(58) Field of Search .................. 623/16, 17, 17.11, 623/17.15, 17.16; 606/61

(56) References Cited

U.S. PATENT DOCUMENTS

| | | | |
|---|---|---|---|
| 5,375,823 A | * | 12/1994 | Navas .......................... 623/17 |
| 5,413,602 A | * | 5/1995 | Metz-Stavenhagen ........ 623/17 |
| 5,571,192 A | * | 11/1996 | Schönhöffer | |
| 5,683,394 A | | 11/1997 | Rinner | |
| 5,702,451 A | * | 12/1997 | Biedermann et al. ......... 623/17 |
| 5,800,547 A | * | 9/1998 | Schafer et al. ................ 623/17 |
| 5,800,550 A | * | 9/1998 | Sertich ......................... 623/17 |
| 5,888,223 A | * | 3/1999 | Bray, Jr. ....................... 623/17 |
| 5,961,516 A | * | 10/1999 | Graf | |
| 6,019,792 A | * | 2/2000 | Cauthen ....................... 623/17 |

FOREIGN PATENT DOCUMENTS

| | | |
|---|---|---|
| DE | 0697200 | 2/1996 |
| WO | 9715246 | 5/1997 |
| WO | 9802117 | 1/1998 |

* cited by examiner

Primary Examiner—Michael J. Milano

(57) ABSTRACT

A device for connecting vertebrae of the vertebral or spinal column through an implant to be arranged between the vertebrae. The implant has at least one hollow space and openings to allow bone tissue formed for connecting the vertebrae to grow into the implant. The implant includes a connecting portion to be placed against exposed soft bone tissue and at least one spacer portion protruding from the connecting portion to be placed against hard bone tissue.

14 Claims, 4 Drawing Sheets

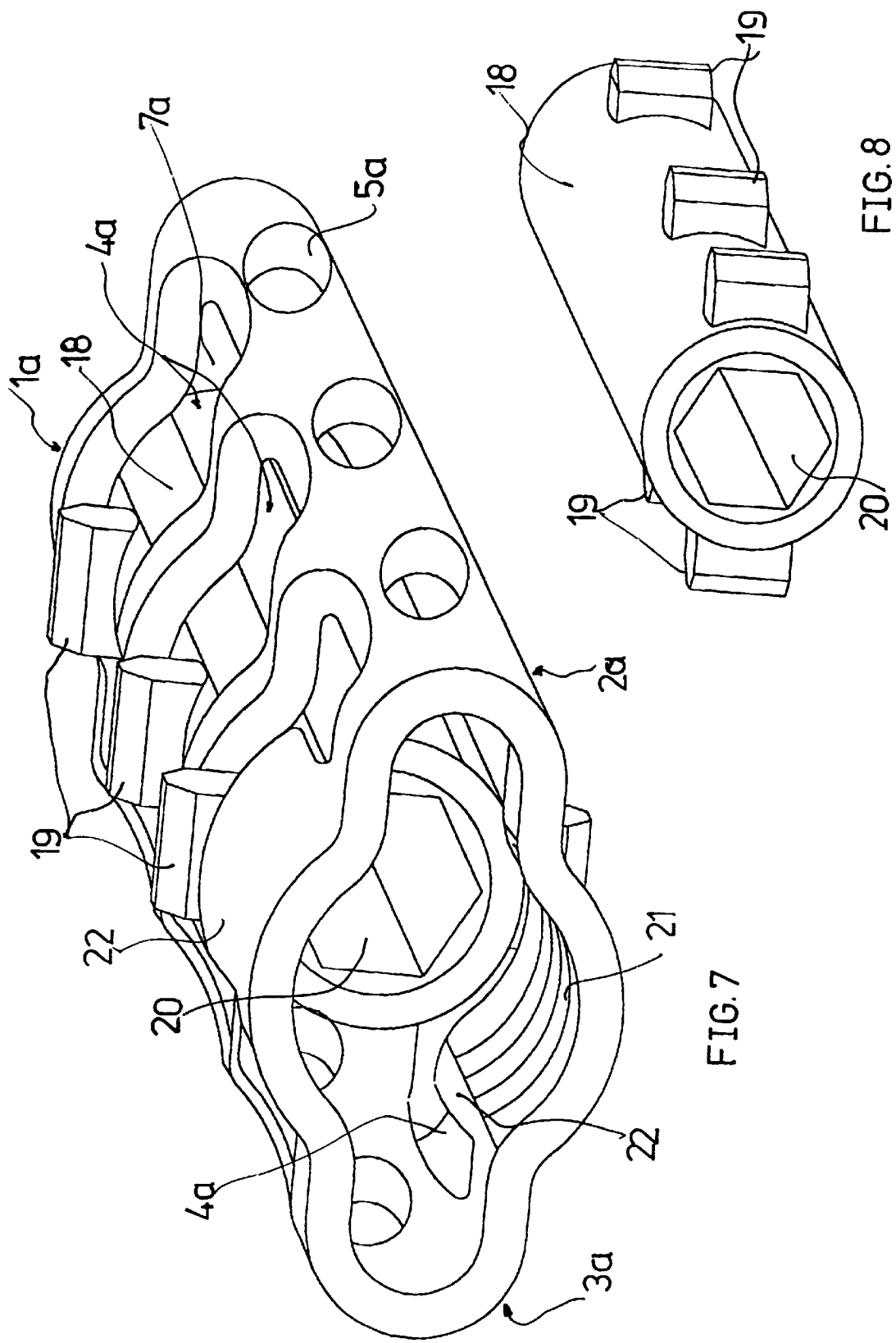

DEVICE FOR CONNECTING VERTEBRAE OF THE VERTEBRAL COLUMN

BACKGROUND OF THE INVENTION

1. Field of the Invention

The present invention relates to a device for connecting vertebrae of the vertebral or spinal column through an implant to be arranged between the vertebrae. The implant has at least one hollow space and openings to allow bone tissue formed for connecting the vertebrae to grow into the implant.

2. Description of the Related Art

When vertebrae are connected, for example, after an intervertebral disk resection, such an implant stabilizes the vertebral column as long as not sufficient connecting bone tissue has formed.

Implants having a cylindrical configuration are known in the art. These implants are provided with an external thread which can be screwed into a prepared threaded bore which has threaded portions in the vertebrae to be connected and located opposite at a distance from each other. When the threaded portions are prepared, the hard bone tissue layer is removed to such an extent that the cylindrical implants come over a portion of their circumference in contact with the underlying soft bone tissue. It is only the soft bone tissue which is capable of forming connecting bone tissue which can grow through openings in the cylinder wall of the implant and can extend through the implant.

Also known in the art are implants which have a parallelepiped-shaped configuration. When these implants are implanted, appropriate cuts have to be prepared in the oppositely located end faces of the vertebrae in order to make it possible that the exposed soft bone tissue forms connecting tissue which can grow through the implant.

SUMMARY OF THE INVENTION

It is the primary object of the present invention to provide a novel device for connecting vertebrae of the vertebral column of the above-described type which, compared to conventional devices, better stabilizes the vertebral column during the growth of the connecting bone tissue and ensures a more exact positioning of the vertebrae within the vertebral column.

In accordance with the present invention, the implant includes a connecting portion to be placed against exposed soft bone tissue and at least one spacer portion protruding from the connecting portion to be placed against hard bone tissue.

The implant according to the present invention makes it possible that a vertical load can be placed on the vertebral column, wherein the spacer portions resting against the hard bone tissue ensure that the vertebrae maintain their required positions within the vertebral column. In implants according to the prior art, it can easily happen that the implant is pressed into the soft bone tissue and the distance between the vertebrae is undesirably reduced.

In accordance with a preferred embodiment of the invention, the connecting part has an essentially rotationally symmetrical configuration, for example, in the form of a cylinder or a conical section. In that case, the work to be carried out on the bone for exposing the soft bone tissue can be carried out with a drilling or milling cutting tool, wherein the dimensions of the drilled or cut areas formed as a result are essentially determined by the dimensions of the tool. In order to work on the bone, the tool merely has to be advanced by a required distance and no further movement of the tool is required for carrying out the work.

In accordance with a preferred feature, the spacer portions are constructed as spacer wings which extend especially diametrically oppositely from the connecting portion. While the connecting portion is in contact with soft bone tissue and extends into a drilled or cut area, the two spacer wings extending on both sides of the connecting portion rest against the hard bone tissue of the upper and lower vertebrae which is located adjacent the respective drilled or cut area.

In accordance with another embodiment of the invention, the connecting portion and at least one spacer portion taper corresponding to the vertebrae which are arranged inclined relative to each other. This embodiment is provided for connecting those vertebrae which are part of the curved portions of the vertebral column.

The hollow space mentioned above may extend into the spacer portion so that connecting bone tissue can also grow into the spacer portion.

In accordance with a preferred feature, the implant is formed as a hollow body with walls for forming openings in the manner of a cage. In particular, the connecting portion has opening slots which extend transversely of the rotational axis direction of the implant. The connecting bone tissue which is formed penetrates through these opening slots into the hollow body and engages behind the walls of the hollow body.

The opening slots may extend beyond the connecting portion into the spacer portions. In addition, the spacer wings may at their wing ends be provided with cutouts, so that connecting bone tissue can also grow into the spacer portions.

In accordance with another preferred embodiment of the invention, the hollow body has on one end face an end wall particularly provided with cutouts, wherein the hollow body is open at the other end face. Such a hollow body can be inserted with the closed end wall side facing forward into the intermediate space between the vertebrae to be connected, wherein, for example, support tools can be inserted into the hollow body of the implant through the other open end face. The end wall also serves to secure filling material which can be filled in order to facilitate the growth of bone tissue into the hollow body.

In accordance with a further development of the invention, a locking device is provided for securing the implant transversely of the longitudinal direction of the vertebral column, wherein the locking device ensures that the implant cannot move out of the intermediate space between the vertebrae to be connected. Such a locking device may include an insert which can be introduced into the implant and which has a hook-type device which engages especially into the soft bone tissue.

In accordance with a preferred embodiment, the hook-type device has hook portions which are arranged on an insert body which is rotatable in the implant in the manner of a cylinder lock, wherein the hook-portions can be turned through the opening slots into the soft bone tissue. Such an insert with hook portions can be inserted into the implant, wherein the hook portions move within the spacer wings. The opening slots extending up to the spacer wings ensure that when the insert body is turned the hook portions can protrude through the opening slots into the soft bone tissue and provide a hook-like connection of the implant in this manner.

The insert can be secured in the implant between the end wall mentioned above and a locking member which can be mounted on the other end face, wherein the locking member preferably used is a headless screw which can be retracted in the implant.

In accordance with an advantageous feature, the insert can be secured in the implant with a predetermined play which is so small that it does not impair the precise positioning of the vertebrae, wherein, however, slight movements of the locking insert hooked into the soft bone tissue promote the growth of connecting bone tissue.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

BRIEF DESCRIPTION OF THE DRAWING

In the drawing:

FIG. 7 is a perspective view of another embodiment of the implant according to the present invention which includes a locking insert; and FIG. 8 is a perspective view of the locking insert used in the implant of FIG. 7.

DESCRIPTION OF THE PREFERRED EMBODIMENTS

Figure 1:
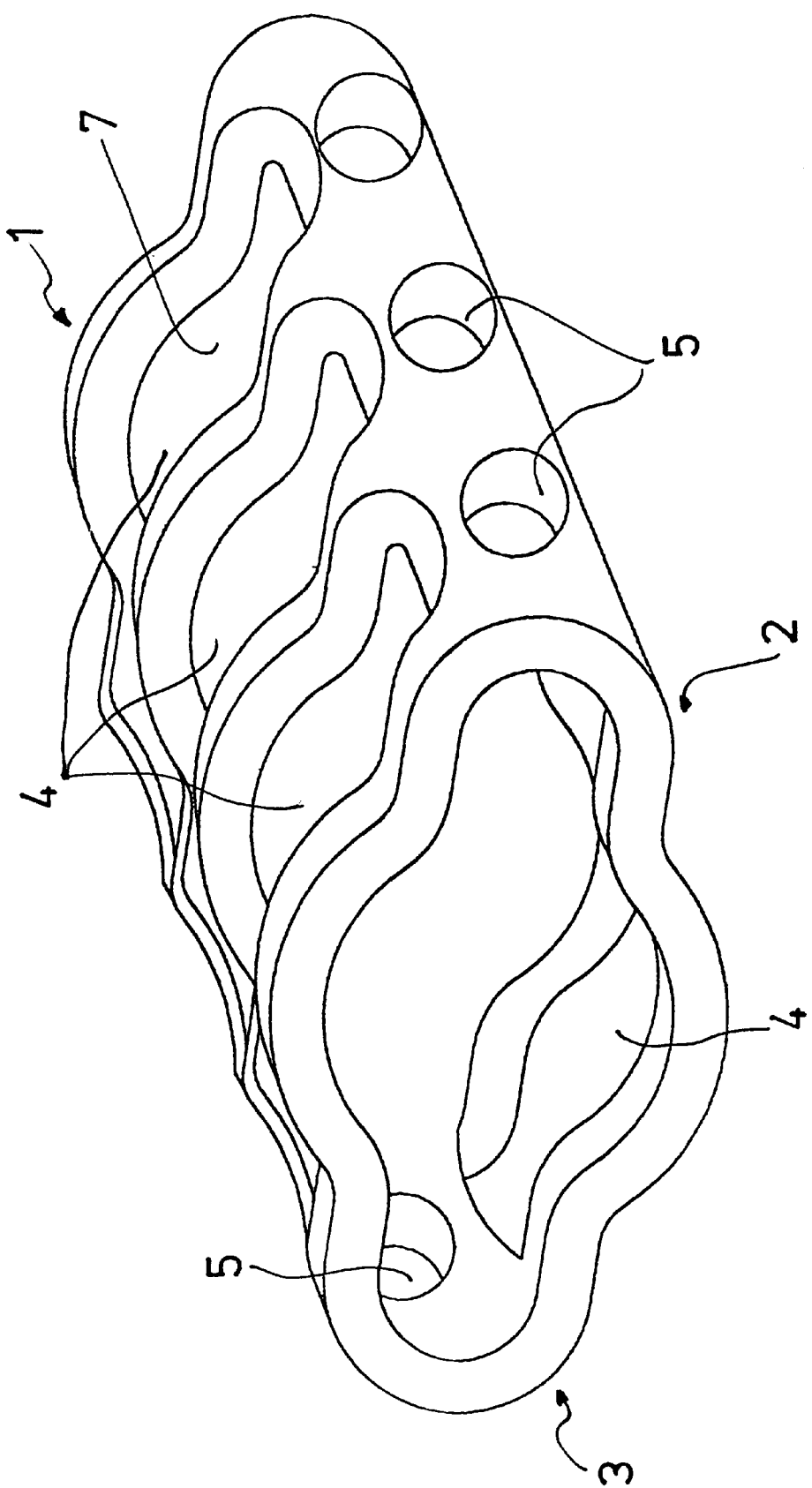
FIG. 1 is a perspective view of the implant according to the present invention.
Figure 2:
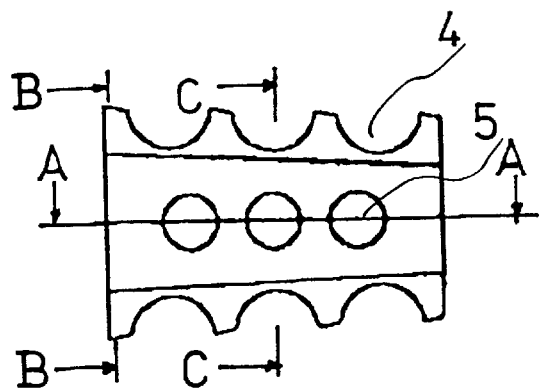
FIG. 2 is a side view of the implant of FIG. 1.
Figure 3:
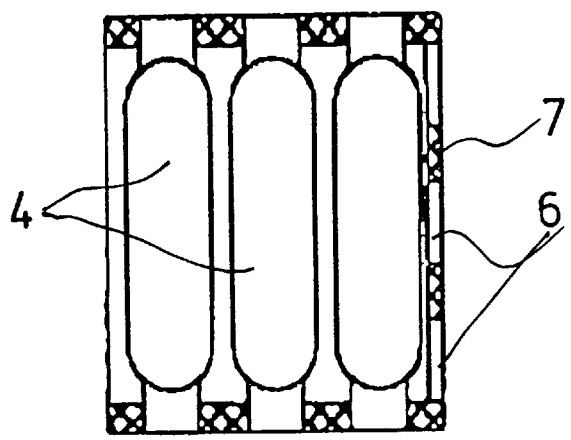
FIG. 3 is a sectional view of the implant of FIG. 1 taken along sectional line A—A of FIG. 2.
Figure 4:
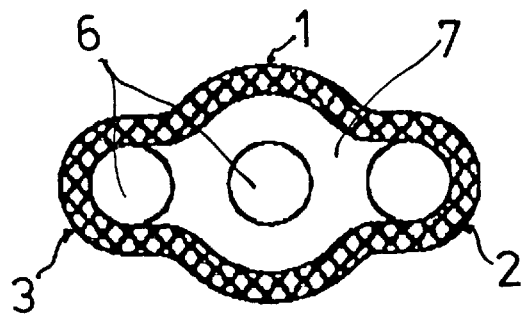
FIG. 4 is a sectional view of the implant of FIG. 1 taken along sectional line B—B of FIG. 2.

FIGS. 1 through 6 of the drawing show a hollow body implant with a connecting portion 1 having an approximately cylindrical configuration and two spacer wings 2 and 3 extending diametrically from the connecting portion 1.

The longitudinal walls of the hollow body implant are perforated in the form of a cage, wherein particularly oppositely located opening slots 4 are provided which extend transversely of the longitudinal axis of the connecting portion 1.

For clarity's sake, the slots 4 are illustrated only partially at the bottom side of the hollow body.

As can be seen in the drawing, the slots 4 not only extend within the wall of the connecting portion 1, but also in the spacer wings 2 and 3.

Cutouts 5 are provided at the ends of the spacer wings 2 and 3.

The hollow body implant is opened at one end face thereof. The end face located opposite the open end face is provided with an end wall 7 having cutouts 6.

Figure 5:
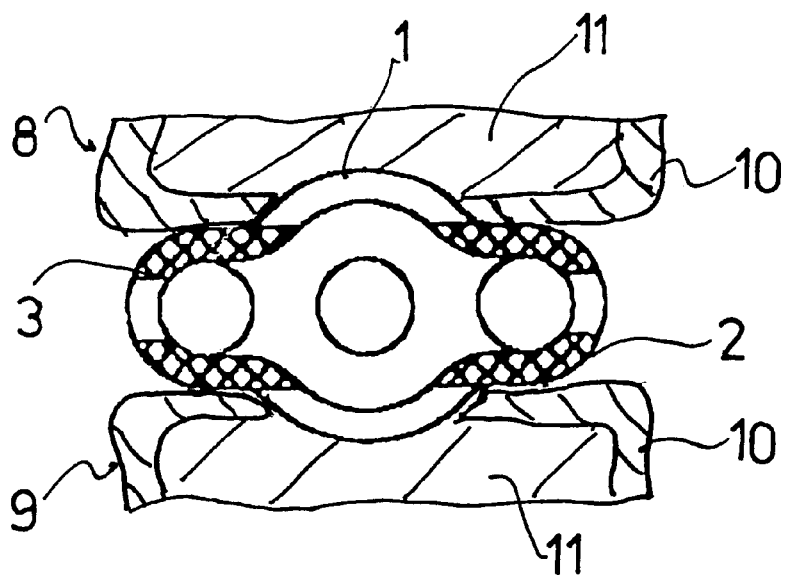
FIG. 5 is a sectional view of the implant of FIG. 1 taken along sectional line C—C of FIG. 2, shown arranged between two vertebrae.
Figure 6:
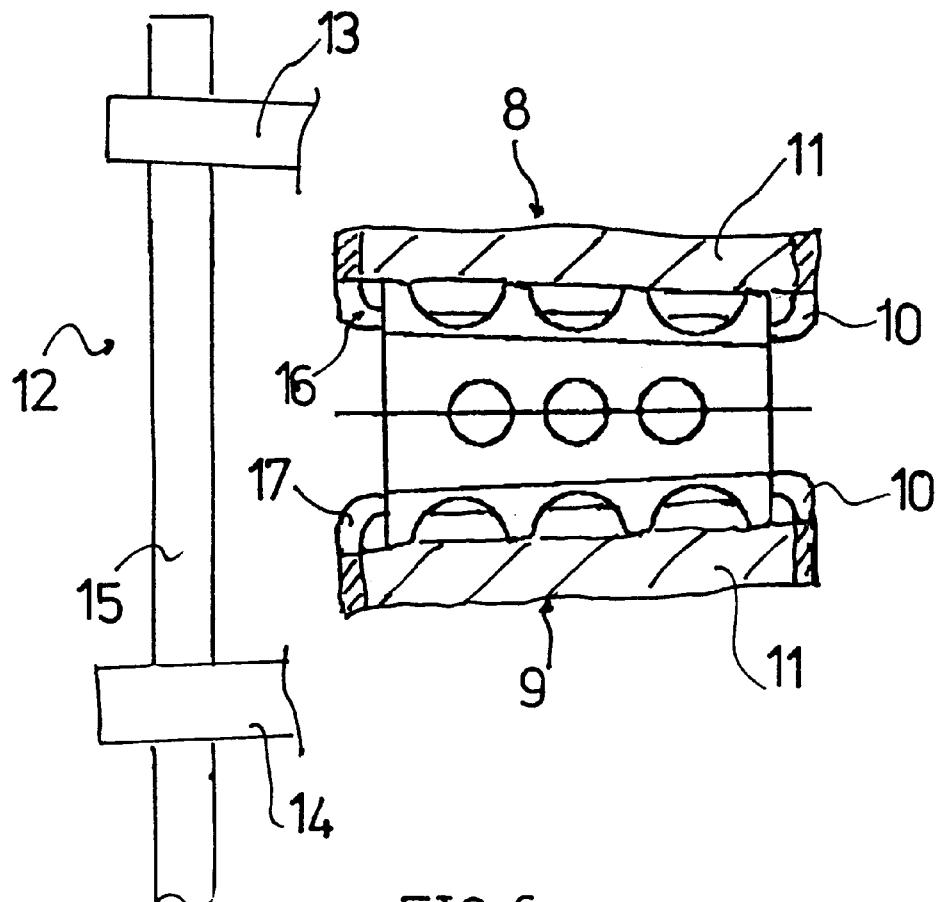
FIG. 6 is a side view corresponding to FIG. 2, showing the implant arranged between two vertebrae positioned by a support device.

Referring now particularly to FIGS. 5 and 6, sections of vertebrae to be connected are denoted by reference characters 8 and 9. The vertebrae have an outer hard bone tissue layer 10 and a soft bone tissue 11 underneath the hard bone tissue.

For placing the implant between the vertebrae 8 and 9, the vertebrae are positioned at a distance from each other and include relative to each other through a schematically illustrated support member 12, wherein the positioning corresponds to the intended position of the vertebrae in a curved portion of the vertebral column. The support member 12 has support parts 13 and 14 which can be mounted on the vertebrae 8 and 9 through screw connections, not illustrated and described in detail, wherein the support parts 13 and 14 can be mounted on a support beam 15 through suitable fastening devices.

When the vertebrae 8 and 9 are secured in this manner, the vertebrae are worked on by means of a slightly conical milling cutter which is advanced between the vertebrae in the direction of its axis of rotation, wherein, in accordance with the dimensions of the milling cutter, oppositely located recesses 16 and 17 are formed in the vertebrae 8 and 9 where the soft bone tissue 11 is exposed.

After the recesses 16 and 17 have been formed, the implant can be inserted in the direction of the longitudinal axis of the connecting portion 1 into the intermediate space between the vertebrae 8 and 9 which are inclined relative to each other, wherein, as can be seen in FIGS. 5 and 6, the connecting portion 1 comes with the greatest portion of its exposed circumference in contact with the soft bone tissue 11. The spacer wings 2 and 3 rest against hard bone tissue 10 which is less resilient as compared to the soft bone tissue 11. This makes it possible to ensure that the described implant can maintain the required distance between the vertebrae 8 and 9 even when a relatively high vertical load acts on the vertebral column.

In the illustrated embodiment, the diameter of the conical connecting portion varies approximately between 8.5 and 7.5 mm. Also in the illustrated embodiment, the thickness of the spacer wings 2 and 3 which determines the distance between the vertebrae 8 and 9 is approximately between 5 and 4 mm. An implant having these dimensions can be used for connecting vertebrae in the neck region.

After the implantation of the implant, the soft bone tissue 11 forms additional connecting bone tissue which grows through the slots 4 from both sides into the hollow body and extends through the hollow body of the implant, wherein, as a rule, the bone tissue grows completely through the hollow body and extends across the intermediate space between the vertebrae 8 and 9. The connecting bone tissue can spread out in the entire hollow space of the implant, wherein it can also grow through the cutouts 5 and 6. Without growing across the intermediate space between the vertebrae 8 and 9, the connection between the vertebrae 8 and 9 can also be produced alone by bone tissue which grows into the hollow body and engages behind the walls of the hollow body.

As long as the bone tissue connecting the vertebrae has not yet been formed, the hollow body implant ensures a stabilization of the vertebral column, wherein especially vertical forces are absorbed by the implant.

Referring now to FIGS. 7 and 8, those parts which are the same or act equally as those described in connection with the embodiment of FIGS. 5 and 6 are provided with the same reference characters except that the letter a is added.

FIG. 8 shows a cylindrical locking insert 18 which can be inserted into a connecting portion 1a of a hollow body implant with opening slots 4a and spacer wings 2a and 3a and can be turned into the connecting portion in the manner of a cylinder lock. Hook portions 19 protrude diametrically from the cylindrical insert 18.

A hexagonal cutout 20 is provided at the end face of the cylindrical insert 18. In contrast to the hollow body implant of FIGS. 1 to 6, the implant body shown in FIG. 7 includes a thread 21 which is formed in a projection 22 which partially protrudes into one of the slots 4a.

In the position illustrated in FIG. 8, the cylindrical insert 18 can be inserted into the hollow body implant, wherein the hook portions 19 move within the spacer wings 2a and 3a.

An end wall 7a forms a stop for the cylindrical insert 18.

By rotating the cylindrical insert 18 by means of a hexagonal tool engaging in the hexagonal cutout 20, the hook portions 19 can be moved into the position shown in FIG. 7 in which they extend through the slots 4a and protrude from the hollow body implant. When the implant is arranged between two vertebrae in the manner illustrated in FIGS. 5 and 6, the hook portions 19 protrude into and hook into the soft bone tissue. The cylindrical insert 18 turned into the position shown in FIG. 7 can be secured within the hollow body implant by means of a preferably headless screw which can be screwed into the thread 21. The insert could also be secured in a more simple manner by clamping the insert in the hollow body, for example, by providing the hook portions 19 with guide stops to be guided in the slots 4a.

The cylindrical insert 18 can also be secured in such a way that a certain play of the insert 18 within the hollow body remains, so that the bone growth is stimulated by slight movements of the hook portions 19 made possible by this play.

By means of the hook portions 19 engaging into the soft bone tissue, the hollow body implant is secured between the vertebrae in the direction extending perpendicularly of the longitudinal axis of the vertebral column, so that an additional stabilization of the vertebral column is ensured.

In the illustrated embodiment, the width of the hook portions 19 is significantly smaller than the width of the slots 4a, so that sufficient intermediate space remains to permit connecting bone tissue to grow in, wherein, in this case, the bone tissue can grow around the cylindrical insert. However, it is also conceivable to provide the cylindrical insert itself with openings and hollow spaces into which the connecting bone tissue can grow.

In contrast to the hook portions 19 shown in the drawing, hook portions with lateral cutting edges could be provided which facilitate the penetration into the soft bone tissue when the cylindrical insert 18 is turned.

In order to provide additional space for bone tissue to grow in, the insert may also have cutouts in several locations.

While specific embodiments of the invention have been described in detail to illustrate the inventive principles, it will be understood that the invention may be embodied otherwise without departing from such principles.

What is claimed is:

1. A device for connecting vertebrae of the vertebral column comprised of an implant adapted to be placed between the vertebrae, wherein the implant has a hollow space and openings for permitting bone tissue to grow therethrough for connecting the vertebrae, the implant further comprising a hollow connecting portion having sides adapted to be placed against exposed soft bone tissue, wherein the connecting portion has an essentially rotationally symmetrical configuration having an axis of symmetry adapted to extend transversely of a longitudinal direction of the vertebral column and spacer wings projecting from the connecting portion and adapted to be placed against hard bone tissue, wherein the spacer wings extend diametrically from the connecting portion, and wherein each of the sides adapted to be placed against exposed soft bone tissue has a plurality of opening slots adapted to be penetrated by bone tissue, the opening slots having longitudinal axes, the longitudinal axes extending transversely of the axis of symmetry.

2. The device according to claim 1, wherein the connecting portion and the spacer wings are tapered corresponding to vertebrae arranged inclined relative to each other.

3. The device according to claim 1, wherein the hollow space extends into the spacer wings.

4. The device according to claim 1, wherein the implant is comprised of a hollow body having perforated walls in the form of a cage.

5. The device according to claim 1, wherein the opening slots extend beyond the connecting portion into the spacer wings.

6. The device according to claim 1, wherein the spacer wings have ends provided with cutouts.

7. The device according to claim 4, wherein the hollow body has an end wall provided with cutouts on one end face thereof and wherein another end face thereof is open.

8. The device according to claim 1, further comprising a locking device for securing the implant transversely of the longitudinal direction of the vertebral column.

9. The device according to claim 8, wherein the locking device comprises an insert insertable into the implant, and wherein the insert has a hooking device adapted for engagement in the soft bone tissue.

10. The device according to claim 9, wherein the hooking device comprises hook portions provided on the insert which is rotatable into the implant in the manner of a cylinder lock.

11. The device according to claim 10, wherein the hook portions are configured to be turnable through the opening slots into the soft bone tissue.

12. The device according to claim 9, wherein the locking insert is mounted in the implant between an end wall of the implant and a locking member mounted on an opposite end face of the implant.

13. The device according to claim 12, wherein the locking member is comprised of a headless screw configured to be retractable in the implant.

14. The device according to claim 9, wherein the locking insert is secured in the implant with a predetermined play.

* * * * *